(12) United States Patent
Prohaska et al.

(10) Patent No.: US 7,601,250 B2
(45) Date of Patent: *Oct. 13, 2009

(54) HYBRID FILM TYPE SENSOR

(75) Inventors: Otto J. Prohaska, Seymour, CT (US);
Anthony B. LaConti, Lynnfield, MA (US); Jose D. Giner, Brookline, MA (US); Mourad Manoukian, Watertown, MA (US)

(73) Assignee: PerkinElmer LAS, Inc., Boston, MA (US)

( * ) Notice: Subject to any disclaimer, the term of this patent is extended or adjusted under 35 U.S.C. 154(b) by 909 days.

This patent is subject to a terminal disclaimer.

(21) Appl. No.: 10/987,825

(22) Filed: Nov. 12, 2004

(65) Prior Publication Data

US 2005/0126930 A1    Jun. 16, 2005

Related U.S. Application Data

(63) Continuation of application No. 10/298,323, filed on Nov. 18, 2002, now Pat. No. 6,936,147, which is a continuation-in-part of application No. 09/444,334, filed on Nov. 19, 1999, now abandoned.

(51) Int. Cl.
*G01N 27/407* (2006.01)

(52) U.S. Cl. .................................. 204/432; 204/424

(58) Field of Classification Search .............. 204/412, 204/415, 424, 431, 432
See application file for complete search history.

(56) References Cited

U.S. PATENT DOCUMENTS

| | | | | |
|---|---|---|---|---|
| 4,442,841 A | * | 4/1984 | Uehara et al. | 600/360 |
| 4,474,183 A | * | 10/1984 | Yano et al. | 600/353 |
| 4,563,249 A | * | 1/1986 | Hale | 205/793 |
| 4,578,154 A | * | 3/1986 | Kitamura et al. | 205/782.5 |
| 4,729,824 A | * | 3/1988 | Giner | 204/415 |
| 4,812,221 A | | 3/1989 | Madou et al. | |
| 4,820,386 A | | 4/1989 | LaConti et al. | |
| 4,851,104 A | * | 7/1989 | Connery et al. | 204/406 |
| 4,859,307 A | * | 8/1989 | Nishizawa et al. | 204/425 |

(Continued)

OTHER PUBLICATIONS (Polyaniline thin-films for gas sensing), N.E. Agbor et al., 1995 Elsevier Science S.A. pp. 173-179.

(Continued)

*Primary Examiner*—Kaj K Olsen
(74) *Attorney, Agent, or Firm*—St. Onge Steward Johnston & Reens LLC (57) ABSTRACT

A miniaturized gas sensor comprised of thick- or thin-film type electrodes, on a non-conductive supportive substrate, and in contact with a solid ionomer electrolyte, for the detection of toxic gases, i.e., carbon monoxide, and other oxidizable or reducible gases and vapors is described. The all-solid planar sensor cell has two or more film type electrodes arranged on a non-conductive planar surface of a supportive substrate. The electrodes are discrete and in intimate contact with the same solid polymer ionomer membrane. The sensor cell contains no liquid electrolyte and is operated in a constant-voltage, potentiostatic or potentiodynamic mode. A high sensitivity to a select gas or vapor is achieved by a novel three-phase contact area design for a sensing electrode which provides contact with the solid ionomer electrolyte, as well as the gas sample via diffusion openings or holes that penetrate through the supportive substrate.

19 Claims, 3 Drawing Sheets

U.S. PATENT DOCUMENTS

| | | |
|---|---|---|
| 5,331,310 A | 7/1994 | Stetter et al. |
| 5,527,446 A | 6/1996 | Kosek et al. |
| 5,573,648 A | 11/1996 | Shen et al. |

OTHER PUBLICATIONS (The Development of a Thick-Film Electrochemical Sensor and Instrumentation for In-Situ Determination of Carbon Dioxide Pressure ($pCO_2$) In The Marine Environment), M.R. Creasey et al., University of Southampton, U.K., Electronic Engineering in Oceanography, Jul. 19-21, 1994, Conference Publication No. 294 IEE 1994.

(Electron theory of thin-film gas sensors) Helmut Geistlinger, 1993 Elsevier Sequoia pp. 47-60.

(A Practical Reference Electrode) J. Giner, Pratt & Whitney Aircraft, Division of United Aircraft Corporation, East Hartford, CT.

(Design and application of thick-film multisensors) N. Hampp et al., 1992 Elsevier Sequoia pp. 144-148.

(Thin Film Porous Membranes for Catalytic Sensors) R.C. Hughes, et al., 1997 International Conference on Solid-State Sensors and Actuators Chicago, Jun. 16-19, 1997.

(Amperometric Gas Sensor of Thin Gold Film Electrode Ion-Plated on Gas Permeable Membrane for Detection of Arsine and Silane) Toru Ishiji et al., pp. 1019-1020.

(A Solid-state pH sensor based on a Nafion-coated iridium oxide indicator electrode and a polymer-based silver chloride reference electrode) Patrick J. Kinlen et al., 1994 Elsevier Science pp. 13-25.

(Multifunctional Sensors Based on Ceramic Electrolytes) Meilin Liu et al., Georgia Institute of Technology, Atlanta, Georgia pp. 421-427.

(The thick-film route to selective gas sensors) F. Menil et al., 1995 Elsevier Science S.A. pp. 415-420.

(Properties of vanadium oxide thin films for ethanol sensor) G. Micocci et al., J. Vac. Sci. Technol. A 15(1), Jan./Feb. 1997 American Vacuum Society.

(An Integrated Multi-Element Ultra-Thin-Film Gas Analyzer) N. Najuh et al., Solid-State Sensor and Actuator Workshop Proc. 5.

(Preparation of thin gold-film electrode for an electrochemical gas sensor for phosphine and arsine) Nobuo Nakano, et al., 1994 Elsevier Science S.A. pp. 51-55.

(A Study of the Surface Sensitivity of Tin Oxide Sensors To Carbon Monoxide and Dioxide) Dario Narducci et al., Dept. of Physical Chemistry & Electrochemistry v. C. Golgi, 19 I-20133 Milano (Italy).

(Thick-Film Solid Polymer Ionomer Sensor Cell and Sensor) Otto Prohaska et al., Giner, Inc. Disclosure No. I-97-013 date Nov. 5, 1997 pp. 1-30.

(UV-Polymerizable Screen-Printed Enzyme Pastes) Ingrid Rohm, et al., 1995 American Chemical Society Analytical Chemistry, vol. 67, No. 13, Jul. 1, 1995, Anal. Chem. 1995, 67,2304-3207.

(CO-Sensor for domestic use based on high temperature stable $Ga_2O_3$ thin films), T. Schwebel, et al., 1997 International Conference on Solid-State Sensors and Actuators Chicago, Jun. 16-19, 1997.

(A Low-Power CMOS Compatible Integrated Gas Sensor Using Maskless Tin Oxide Sputtering) Lie-yi Sheng, et al., 1997 International Conference on Solid-State Sensors and Actuators Chicago, Jun. 16-19, 1997 pp. 939-942.

(Platinum Thin Films and Next-Generation Micromachined Sensors) John Staley, et al., Sensors Apr. 1996.

(An amperometric carbon monoxide sensor based on the steady-state difference response technique) Y. Tan et al., 1995 Elsevier Science S.A. pp. 113-121.

(A Novel Semiconductor No Gas Sensor Operating At Room Temperature) Zhang Wenyi et al., 1997 International Conference on Solid-State Sensors and Actuators, Chicago, Jun. 16-19, 1997.

(Environmental gas sensing) Noboru Yamazoe et al., 1994 Elsevier Science S.A. pp. 95-102.

(Life-elongation mechanism of the polymer-electrolyte lamination on a CO sensor) Ayumu Yasuda, et al., 1994 Elsevier Science S.A. pp. 229-236.

\* cited by examiner

HYBRID FILM TYPE SENSOR

PRIORITY APPLICATION

This application is a continuation patent application of U.S. Patent Application Ser. No. 10/298,323, now U.S. Pat. No. 6,936,147, for a "Hybrid Film Type Sensor" filed Nov. 18, 2002, which is a continuation in part of U.S. application Ser. No. 09/444,334 filed Nov. 19, 1999 now U.S. Pat. No. 6,564,341.

FIELD OF THE INVENTION

The invention is directed toward a sensor having improved repeatability and efficiency.

BACKGROUND OF THE INVENTION

Film based techniques have generally been investigated for a wide variety of sensors, as reported by Wenyi et al., 1997; Hughes et al., 1997; Staley, 1996; Agbor et al., 1995; Tan and Tan, 1995; Menil et al., 1994; Kunnecke et al., 1994; Creasey and Varney, 1994; Geistlinger, 1993; Ishiji et al., 1993; Najafi et al., 1992; Hampp et al., 1992; Nakano and Ogawa, 1994; Yamazoe and Miura, 1994; and, Madou and Otagawa, 1989. While solid-state gas sensors may have the advantage of being able to operate at elevated temperatures, they also may have the disadvantages of slow response and recovery time and a high internal operating temperature as reported by Liu et al., 1993; and Narducci et al., 1993. More recent literature (Schwebel et al., 1997; Sheng et al., 1997; Micocci et al., 1997) eludes to more substantial development work yet to be done.

In Kinlen et al., 1994, a Nafion®-coated metal oxide pH sensor is generally characterized as having sputtered iridium oxide sensing and silver/silver chloride reference electrodes on alumina ceramic substrates. Nafion may have been used as a cation-selective ionomer coating in order to decrease the oxidation-reduction error typically affecting the performance of metal oxide pH electrodes. In Yasuda et al., 1994, the use of Nafion as polymer-electrolyte for a thin-film CO sensor is generally described with macro-sized, sputtered Pt sensing and counter electrodes and a smaller, sputtered Au electrode as a reference electrode. A 5 wt % n-propyl alcohol solution of Nafion (DuPont, 1100 EW) may be used to form the polymer electrolyte film over the electrodes by casting. The polymer is usually washed and protonated in aqueous sulfuric acid prior to casting. A theorized lifetime of this sensor is normally less than one month. During this time, the CO oxidation current typically decreases steadily down to a few percent of its original value without any period of stable measurement signal. The lifetime of the device may be extended up to three years by laminating the polymer electrolyte layer with a cast perfluorocycloether-polymer film in order to keep the CO permeability coefficient through Nafion constant. Theoretical calculations often reflect the drift rate of the signal could be significantly reduced under these conditions.

A description of typical state-of-the-art hydrated solid polymer electrolyte or ionomer sensors and sensor cells is generally described by Kosek et al. U.S. Pat. No. 5,527,446; LaConti and Griffith, U.S. Pat. No. 4,820,386; Shen et al., U.S. Pat. No. 5,573,648; and, Stetter and Pan, U.S. Pat. No. 5,331,310. These sensor cells, based on hydrated solid polymer electrolyte or ionomer technology, may have several advantages over conventional electrochemical sensor cells. The catalytic electrodes are normally bonded directly to both sides of a proton conducting solid polymer ionomer membrane providing a stable electrode to electrolyte interface. One side of the electrolyte membrane is usually flooded with distilled water, making the sensor cell self-humidifying and independent of external humidity. Since no corrosive acids or bases are generally used in the sensor cell, a lifetime of over 10 years may be experienced for solid polymer ionomer sensor cells. Finally, the sensor cells may be easy to maintain and may be ideal for use in remote, unattended environments because maintenance typically entails little more than addition of water to the reservoir in the sensor housing every several months and monthly calibration checks.

A disadvantage of the state-of-the-art sensors described above may be that the signal-to-noise ratio is not be conducive to detection of very low concentrations (parts per billion, ppb) of important environmental and biomedical gases and vapors. Also, response time may be relatively slow, and reproducibility between sensors and sensor cells may be difficult to achieve. Also, they are relatively costly.

Recently, miniaturized thick- and thin-film type sensors have been developed where the solid ionomer membrane often acts as a conduit between the gas to be detected (sample gas) and the sensing electrode (Yasuda et al., 1994). The sample gas usually permeates through the membrane itself where a 3-phase contact area is established. A disadvantage with this configuration may be that the solid ionomer membrane water content often controls the gas permeation rate as well as proton conductivity. As the humidity increases, the membrane water content typically increases. This may cause an increase in the gas diffusion rate as well as proton conductivity and sensor signal response. A method for controlling or fixing the water content of the membrane may be to have a water reservoir on the back side of the membrane, directly opposite to where the film type electrodes and non-conductive supportive substrate are located. However, the back side of the membrane is often required to be free of liquid so that the sample gas can diffuse through the membrane to the sensing electrode.

U.S. Pat. No. 4,812,221 to Madou et al. ("Madou") typically relates to a gas sensor having a porous member located in a passage adjacent and generally in contact with a sensing electrode. The pore size of the porous member may be controlled by varying the processing parameters, such as current, hydrogen fluoride concentration, and the like. In addition, Madou appears to indicate a number of other steps for providing the gas sensor, such as sizing the pores in the porous membrane, sizing the pores of the sensing electrode, and selecting the materials of the electrodes. A problem often associated with a sensor provided in accordance with Madou is difficulty in repeatability and/or reproducibility due to the numerous variations from one sensor to another. Another difficulty may be problems or costs in manufacturing sensors due to the quantity of steps, where it is often believed that manufacturing becomes more expensive as the quantity of steps is increased. Another possible disadvantage is that the permeability coefficient of the filter in Madou is not disclosed to be utilized for determining the membrane's thickness and other physical characteriztics, which optimizes the sensor's response time. Still a further possible disadvantage is that Madou's filter is inert and does not react, if desired, with the gas that diffuses through the membrane.

What is desired, therefore, is a sensor having improved repeatability. Another desire is to provide a sensor having improved response time. A further desire is to provide a sensor having an improved signal to noise ratio. A still further desire is to provide a sensor that is easy to manufacture with reduced costs while maintaining or improving its operational and manufacturing efficiency.

SUMMARY OF THE INVENTION

This invention is directed toward a controllable and reproducible gas sensor configuration having a three-phase contact area, whereby the sample gas diffuses to the sensing electrode and solid proton conductive membrane through openings, holes or slits that extend through the non-conductive supportive substrate as well as a solid diffusion membrane.

This invention is further directed toward a gas sensor where the gas diffusion process is decoupled from the proton conduction process. Hence, the invention controls gas flow via the holes in the substrate and not merely through the diffusion membrane that is in contact with the sensing electrode, which is known in traditional sensors. Therefore, the invention may use, in addition to the substrate holes, a non-electrolytic or an electrolytic membrane to control gas flow. The gas diffusion is controlled by through openings of known area in the substrate or in the substrate and an additional rate limiting gas diffusion barrier film, eg: polyethylene, while proton conduction takes place only through a proton conductive electrolyte layer, e.g., a Nafion® membrane.

The invention is also directed toward utilizing a method of mass producing film type gas sensors by stacking a number of component layers to form a series of adjacent sensors which are subsequently separated into individual sensors.

The invention is still further directed toward a gas sensor utilized in conjunction with a gas sensor control circuit.

The invention is also directed toward a gas sensor utilized in a gas sensing instrument.

The invention achieves the foregoing and other objects by providing a sensor having a substrate with a first surface and a second surface, a sensing electrode in contact with the substrate, and an opening extending from the first surface to the second surface proximate to the sensing electrode for controlling a gas flow. The invention further includes a gas diffusion membrane being of electrolytic material in contact with the sensing electrode and placed within the opening and between the gases to be detected and sensing electrode. The gas diffusion membrane has a thickness determined from a permeability coefficient of the gas diffusion membrane.

In another embodiment, a polymeric gas diffusion membrane is used instead of an electrolytic membrane, where the polymeric membrane may be non-electrolytic and, therefore, not reacting with the gas and/or sensing electrode.

In a further embodiment, the gas diffusion membrane is made of an electrolytic material where the thickness of the membrane may be optionally determined from the permeability coefficient.

DETAILED DESCRIPTION OF THE INVENTION

The present invention overcomes the limitations of the sensors mentioned above by uniquely combining an advanced solid polymer ionomer membrane configuration with a film type electrode on a non-conductive supportive substrate. The substrate has diffusion openings or holes having a known area which permit easy access of the sample gas, through a diffusion membrane, to a sensing electrode contact area. The sensor configuration provides a three phase contact area at the interface of the membrane, the sensing electrode, and the gas being detected. This design utilizes the precision of solid-state device fabrication techniques to yield inexpensive, low maintenance, highly sensitive, rapidly responsive, and reproducible sensor devices for environmental, industrial, and biomedical monitoring.

Figure 1:
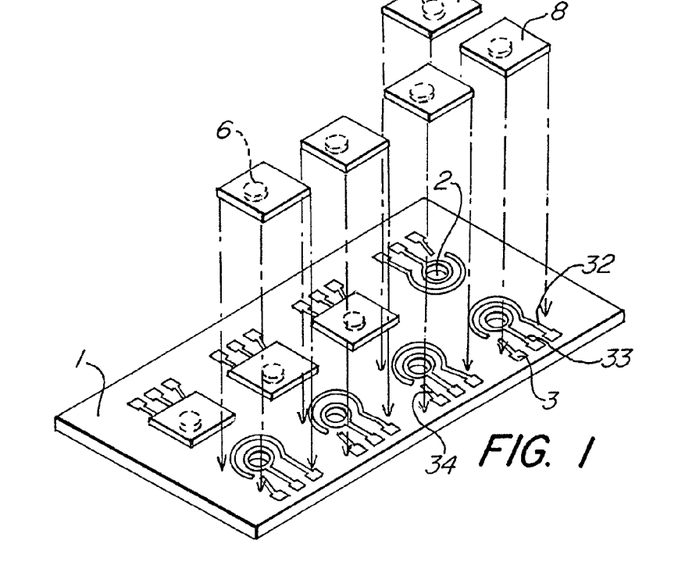
FIG. 1 shows a schematic top view of the non-conductive supportive substrate.

FIG. 1 shows the top view of a substrate (1), which is preferably non-conductive and may be a sheet or film of ceramic or alumina, having holes (2). Holes (2) are shown to be distributed in generally parallel rows but such an arrangement of uniformity is not required for proper operation of the sensor. The distance between holes (2) in the parallel rows and the distance between the rows determine the dimensions of the sensor. In a preferred embodiment, holes (2) are ideally punched in a single step, while the alumina plate is still soft, in the "green" stage of substrate fabrication, prior to high-temperature sintering. In other embodiments, holes (2) are created using laser ablation or use of soluble fillers. In further embodiments, any manner for providing holes (2) is envisioned.

Conducting leads 32, 33, and 34 and thick- and thin-film electrodes are formed on substrate (1) for multiple electrodes. Leads 32-34 may be provided using screen printing or lithographic techniques or any other manner for providing leads 32-34 on substrate (1).

Figure 2:
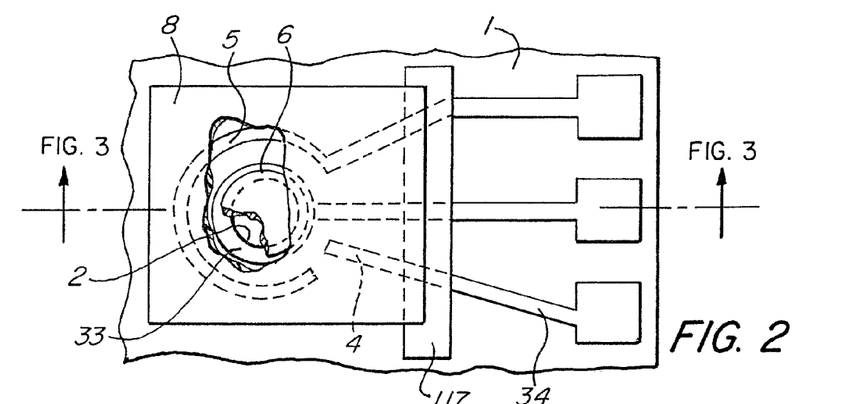
FIG. 2 shows a film type electrochemical sensor cell with Pt/Air ($O_2$) reference.

A typical sensor design utilizing this method is shown in FIG. 2, which has reference electrode (4) and a Pt counter electrode (5). Reference electrode material includes Platinum or Pt/Air ($O_2$) and counter electrode material includes Platinum. The contact for the sensing electrode (6) is a ring concentric to the hole. This ring can be made of smooth, rough or platinized platinum. In other embodiments, this ring may be Platinum, Gold, Titanium, Tantalum, Zirconium, Tungsten, or Niobium. Some platinization of the ring may provide better contact. Simultaneous platinization of electrodes can be performed by customized electrolytic plating on properly masked multi-sensor plates.

The sensing or working electrode (6) may be a disc of Teflon®-bonded or Nafion-bonded platinum or other electro-catalyst. A number of discs are deposited on an ionomer film, such as Nafion electrolyte membrane (8) at uniform distances from each other, for instance, by decal transfer, silk printing, spray painting, artist brush lettering, or by any approach which lends itself to uniform deposition of a design on a transfer substrate without waste. The discs' distances from center to center are the same as for the holes of FIG. 1. The diameter of the sensing or working electrode disc is larger than the diameter of the hole in FIG. 1 to allow for contact between the disc and the sensing electrode support ring of FIG. 2. Instead of a single large hole per sensor of FIG. 1 (which requires the use of the substrate to control diffusion of the analyte), a series of smaller openings may be used, with small enough diameters to control diffusion independently of the analyte flow. The areas of the openings are chosen so as to control diffusion of the sample gas toward the sensor and to maintain a constant diffusion rate independent of any changes in the sample gas flow rate. By using a number of these diffusion-controlling orifices, a reasonably large signal may be obtained. The range for the length to diameter ratio for these orifices is 2/20 with a preferred ratio of 3/10.

Figure 3:
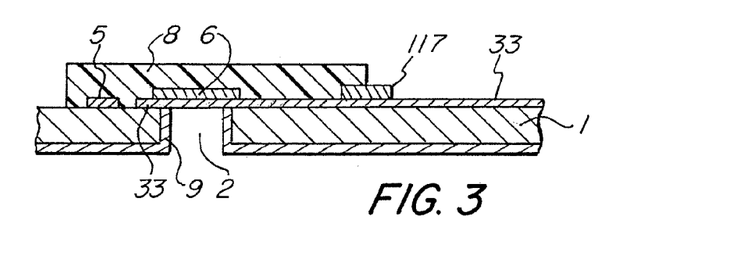
FIG. 3 shows a film type electrochemical sensor cell with a polymeric gas-diffusion layer over the sensing electrode membrane.

Over the empty alumina surface (the surface with no printed leads and electrodes) a gas-permeable diffusion film (9) is deposited. Film (9) is made to conform to the sensing electrode over holes (2), as shown in FIG. 3, or hangs loose over sensing electrode (6). The substrate (with multiple arrays of printed conductors), the Nafion membrane (with multiple sensing electrode discs), and the gas-permeable film are arranged as shown in the schematic representation of FIG. 3. After all the components are unitized, the resulting structure is cut in individual sensor units.

Because holes (2) control the diffusion, or flow, of gas that diffuse toward sensing electrode (6), membrane (9) is of a polymeric material. Polymeric is defined to be either electrolytic, such as an ionomeric film, or non-electrolytic. Depending upon the application or experiment, membrane (9) may be of a non-electrolytic material when no reaction, or interference, is desired between membrane (9) and sensing electrode (6). In other embodiments, membrane (9) may be of an electrolytic material when reaction between membrane (9) and sensing electrode (6) is desired. In further embodiments, membrane (9), whether electrolytic or non-electrolytic, may, in addition to holes (2), provide a second structure to control gas diffusion. However, it is understood that holes (2) provide the primary gas diffusion structure to the invention.

Permeability of membrane (9), which is an indication of the diffusion rate of a gas through membrane (9), may be expressed as a coefficient, which is a function of the gas to be diffused through membrane (9) and the material selected for membrane (9).

In other words, the permeability coefficient is an indication of the amount of molecules that may move through membrane (9) with a certain thickness, at a certain temperature, under a certain pressure, and in a given time. Hence, a user selects membrane (9) for use with the invention. A first step is for the user to determine the gas to be diffused and the type of material, based on reactive properties with the gas, to be used in the sensor. Then, based on the permeability coefficient of the material and gas to be diffused, the user determines the thickness, surface area of membrane (9), and other physical characteristics of membrane (9).

By selecting membrane (9), the sensor is completed quickly and easily, thereby reducing manufacturing costs. Further, the sensor has enhanced repeatability because membrane (9) is generally of a similar material, thickness, surface, area, and permeability coefficient from sensor to sensor. Hence, membrane (9) is controlled during manufacturing in an improved manner over the prior art.

It is understood that the thickness of membrane (9) is merely one physical characteristic that may be determined from the permeability coefficient and that other characteristics may be calculated.

The formula for determining the thickness of membrane (9) based on the permeability coefficient is:

$$i = P_d \times A \times \Delta P/d \text{ or } d = P_d \times A \times \Delta P/I$$

The flux of gas through the gas permeable membrane (9), and thus the measured amount of current i, depends on the difference in partial pressure $\Delta P$ of the gas across the membrane (9). The area A is equal to the geometric sensing electrode area and d is the membrane (9) thickness. $P_d$ is the permeability coefficient.

The formula for determining the volume of gas diffusing through membrane (9), per second, based on the permeability coefficient is:

$$F_d = P_d \times \Delta c$$

where $F_d$ is the flow density, measured in mol/cm² sec, assuming a 1 cm thick membrane, standard pressure of 1 atm, and standard room temperature. $P_d$ is the permeability coefficient, which may be measured in units of cm/sec. $\Delta c = c_1 - c_o$ is the concentration difference across the membrane, measured in mol/cm³, where $\Delta c$ is the difference between the two concentrations on both sides of the membrane. $c_1$ is the concentration of the material inside the membrane, which is preferably located on a surface of the sensing electrode. $c_0$ is the concentration outside of the membrane, which is preferably the gas sample, surrounding air outside the chamber, or the gas flowing through a GC (in which we want to measure how much of a specific gas, for example $H_2S$, is contained in that gas sample).

The formula for determining the concentration of gas within membrane (9) as a function of time based on the permeability coefficient is:

$$c_1(t) = c_0 \times (1 - e^{-t/T})$$

$T = V/(A \times P_d)$ ... is the time constant of the equation above
A is the geometrical area of the membrane
V is the volume of the material in front of the membrane
$P_d$ is the permeability coefficient
In this example $c_1$ is a function of time and changes from zero at $c_1$ (o) to $c_1$ (for t=infinity)=$c_0$ The following is a non-exhaustive list of possible materials and permeability coefficients that may be used for membrane (9):

TABLE 1

| Gas | Temperature deg C. | Permeability coefficient Glassine | Permeability coefficient Polyethylene |
|---|---|---|---|
| Carbon dioxide | 30 | 9.7 | 28.1 |
| Hydrogen sulphide | 30 | 9.7 | 43.0 |
| Oxygen | 30 | 10.5 | 6.9 |
| Nitrogen | 0 | 11.2 | 0.25 |
|  | 30 | 9.4 | 2.1 |
|  | 50 | 9.3 | 7.4 |
|  | 70 | 8.4 | 22.0 |

Units cc × cm × 10¹⁰/sq cm × sec × Δcm Hg at Standard Temperature and Pressure

TABLE 2

| Material | $P_{O_2}$ | $P_{CO_2}$ | Ratio ($CO_2/O_2$) | $P_{H_2O}$ |
|---|---|---|---|---|
| Polyacrylonitrile | 0.0003 | 0.0018 | 6.0 | 300 |
| Polymethacrylonitrile | 0.0012 | 0.0032 | 2.7 | 410 |
| Polyvinylidene chloride | 0.0053 | 0.029 | 5.5 | 1 |
| Barex (Sohio Co.)* | 0.0054 | 0.018 | 3.3 | 660 |
| Polyethylene terephthalate | 0.035 | 0.17 | 4.9 | 175 |
| Nylon 6 | 0.038 | 0.16 | 4.2 | 275 |
| Polyvinyl chloride (unplasticized) | 0.045 | 0.16 | 3.6 | 275 |
| Polyethylene (0.964 density) | 0.40 | 1.80 | 4.5 | 12 |
| Cellulose acetate (unplasticized) | 0.80 | 2.40 | 3.0 | 6,800 |
| Butyl rubber | 1.30 | 5.18 | 4.0 | 120 |
| Polycarbonate | 1.40 | 8.0 | 5.7 | 1,400 |

TABLE 2-continued

| Material | $P_{O_2}$ | $P_{CO_2}$ | Ratio (CO$_2$/O$_2$) | $P_{H_2O}$ |
|---|---|---|---|---|
| Polypropylene (0 907 density) | 2.20 | 9.2 | 4.2 | 65 |
| Polystyrene | 2.63 | 10.5 | 3.8 | 1,200 |
| Neoprene | 4.0 | 25.8 | 6.5 | 910 |
| Teflon | 4.9 | 12.7 | 2.6 | 33 |
| Polyethylene (0.922 density) | | | | |
| Poly (2,6 dimethyl phenylene oxide) | 15.8 | 75.7 | 4.8 | 4,060 |
| Natural rubber | 23.3 | 153 | 6.6 | 2,600 |
| Poly (4 methyl pentene 1) | 32.3 | 92.6 | 2.9 | — |
| Poly dimethyl siloxane | 605 | 3,240 | 5.3 | 40,000 |

Temperature is 30° C. for all of the above
*High acrylonitrile copolymer
Units cc × cm × $10^{-10}$/sq cm × sec × Δcm Hg at Standard Temperature and Pressure

TABLE 3

| Polymer Membrane | $O_2$ Permeability $10^{-16}$ [mol m/s m$^2$ Pa] |
|---|---|
| PTFE. | 0.25 |
| Mylar ® | 0.0063 |
| Nylon 6 | 0.013 |
| PVA10$^{-10}$ | 0.033 |
| PVC | 0.047 |
| Methyl cellulose | 0.233 |
| Cellulose acetate | 0.267 |
| PE, high density | 0.33 |
| Polystyrene | 0.4 |
| Natural rubber | 8 |
| Fluorosilicone | 36.6 |
| PDMS | 167 |

TABLE 4

| | Permeability × $10^{10}$ moles/sec | | |
|---|---|---|---|
| Polymer | $O_2$ | $CO_2$ | $H_2O$ |
| Dimethyl silicone rubber | 804 | 4200 | 50,000 |
| Natural rubber | 32.0 | — | — |
| Polyethylene (low density) | 10.7 | 33.0 | 444 |
| Teflon | 7.6 | 21.0 | 46 |
| Polystyrene | 1.6 | 4.0 | — |
| Polypropylene | 1.34 | 4.5 | 100 |
| Mylar | 0.025 | 0.046 | 70 |

For 1-mil thick membranes, 1 cm$^2$, at room temperature with a differential pressure of 760 mm across the membrane.

The following is a non-exhaustive list of possible materials and thicknesses that may be used for membrane (9):

TABLE 5

Electrode output and response time as a function of cathode area, membrane, and membrane thickness

| Electrode | Membrane | Thickness | Output (air) | 97.5% Response Time (Air→Nitrogen) |
|---|---|---|---|---|
| Galvanic (55-mil cathode) | Teflon | 0.5 mil | 4.40 µa | 2.0 sec |
| " | " | 1.0 mil | 1.63 µa | 8.0 sec |
| | Polypropylene | 0.5 mil | 0.80 µa | 10.0 sec |
| " | " | 1.0 mil | 0.222 µa | 30.0 sec |
| Polarographic (1.0-mil cathode) | Polypropylene | 0.5 mil | 0.80 na | 18.0 sec |
| " | " | 1.0 mil | 0.41 na | 45.0 sec |
| | Teflon | 0.125 mil | 8.3 na | 0.3 sec |
| | Teflon | 0.25 mil | 4.2 na | 0.6 sec |
| | Teflon | 0.375 mil | 3.75 na | 1.0 sec |
| | Teflon | 0.5 mil | 2.70 na | 2.2 sec |
| | Teflon | 0.75 mil | 2.34 na | 7.0 sec |
| | Teflon | 1.0 mil | 1.78 na | 17.0 sec |
| Fermentation (Polarographic with 10-mil cathode) | Special Silicone Composite | | 110 na | 45.0 sec |

The film type sensor configuration described above is integrated with a potentiostat and a voltage of approximately +0.1 V is applied to the Pt sensing electrode with respect to a Pt/Air (O$_2$) reference. This corresponds to an applied potentiostatic voltage of approximately 1.16 V with respect to a normal hydrogen electrode (NHE).

Gas samples of air and 7.4 ppm SO$_2$ in air are introduced into the sampling port of the fixture described above. The gas flow is approximately 60 cm$^3$/min and temperature is approximately 25° C. The sample gas diffuses through the 80-mil hole in the non-conductive substrate and electrochemically reacts at the exposed sensing electrode/solid ionomer electrolyte surface. Humidification is provided by the liquid water in the reservoir which soaks the opposite, or back side of the membrane where the electrode structures are located.

The background response signal with air is 30 nanoamps (nA). The response signal with 7.4 ppm SO$_2$ in air is 135 nA. This corresponds to a net response signal for 7.4 ppm SO$_2$ in air of 105 nA or 14.2 nA/ppm per 80-mil hole. It is possible to increase the magnitude of signal and signal-to-noise ratio by increasing the number of holes in the substrate above the integral sensing electrode structure.

It is also possible, with this configuration, to detect other oxidizable or reducible gases such as CO, NO, NO$_2$, H$_2$S, ozone, CO$_2$, hydrogen, hydrazine, ammonia, HCl, alcohols and acetone.

Figure 4:
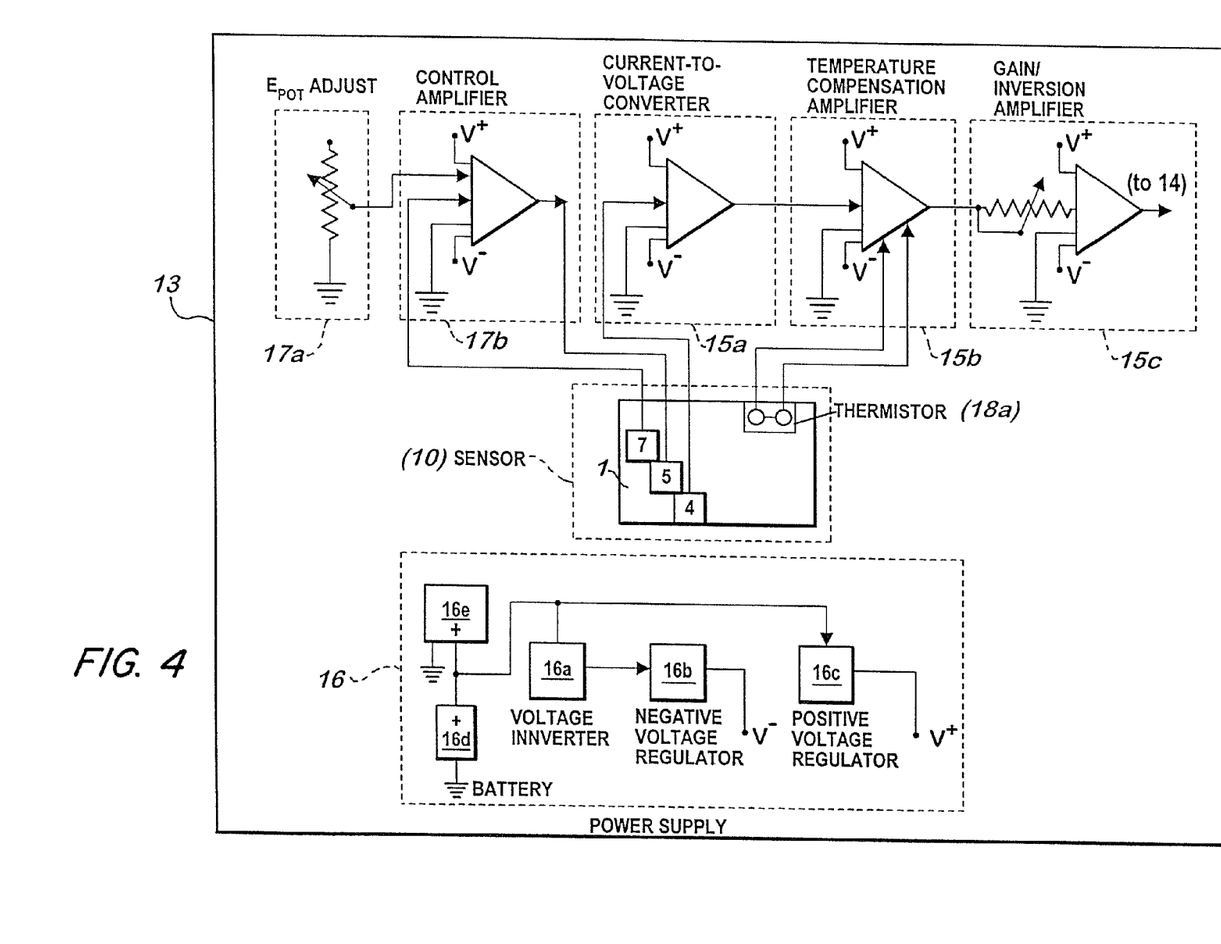
FIG. 4 shows a gas sensor control circuit.
Figure 5:
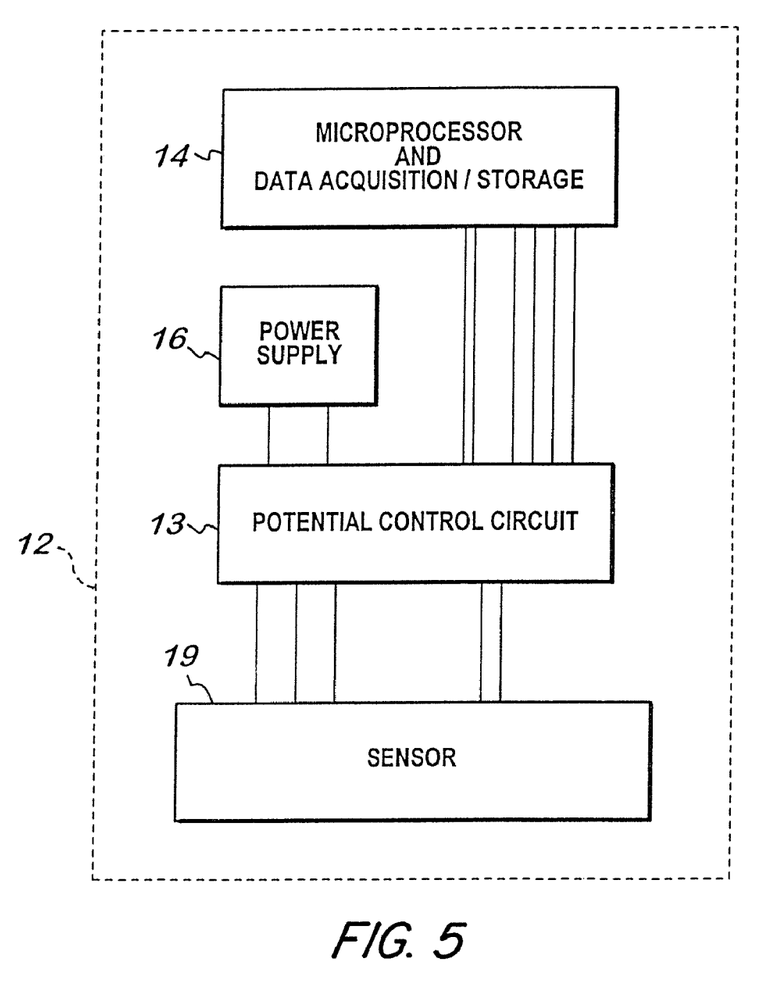
FIG. 5 shows a gas sensor utilized in a gas sensing instrument.

Referring to FIGS. 4 and 5, a block diagram of the sensor control circuit (13) is shown. The sensor control circuit (13) is designed to: 1) control the potential of the sensing electrode (6) at a predetermined voltage (the "potentiostatic voltage", or "$E_{pot}$"); 2) measure the temperature; 3) convert the gas concentration-related current to a temperature-compensated voltage signal; and 4) provide properly amplified voltage to the data acquisition/storage microprocessor (14). An on-board micro power-regulated power supply (16) uses the microprocessor's (14) power supply to provide the required ±3.9 volts for the sensor circuitry. The DC power can be supplied by a 6-V battery (16d) or an AC adaptor (16e).

The control amplifier portion (17b) of the sensor control circuit (13) consists of a micro power operational amplifier (e.g., MAX407 or LM6062). The sensing (6), counter (5) and reference (4) electrode portions of the sensor assembly (1) are in the feedback loop of the control amplifier (17b) as shown in FIG. 4, a standard configuration for potentiostat circuits. An adjustable voltage divider (17a) allows the polarizing voltage ($E_{pot}$) to be set at a predetermined voltage range such as 0 to 50 mV. This signal is compared to the reference electrode (4) voltage (which appears with it at the summing junction) by the control amplifier (17b) of the sensor control circuit (13). The latter adjusts the current through the sensor cell (10) to minimize the difference between the $E_{pot}$ and the reference electrode (4) voltages.

The resulting sensor cell assembly (19) current (flow of electrons from sensing electrode (6) to counter electrode (5)), which is linearly related to the concentration of gas, is transformed into a voltage signal by the current-to-voltage converter (15a). Temperature compensation of the sensor signal is effected in the next stage of amplification (15b) using a thermistor (18a) which is positioned in the gas sensor housing (10). The last stage of amplification (15c) provides, if required, inversion of the voltage signal as well as gain adjustment, to permit calibration for normal variations in sensitivity among sensors. The same type of micro power operational amplifier is used for these stages (15a), (15b), (15c) as for the control amplifier (15b). The transformed current signal is directed to an A/D channel on the data acquisition board of the microprocessor (14).

Power for the sensor control circuit (13) is provided by a Duracell 6-V battery (16d) (PX 28A or 28L) through a micro power-regulated power supply (16). The power supply (16) utilizes a voltage inverter (e.g., ICL 7660) (16a) to convert the positive battery voltage to a negative voltage of the same magnitude, and a positive voltage regulator (e.g., MAX663) (16c) and negative voltage regulator (e.g., MAX 664) (16b) to provide a stable ±3.9 volts.

The film type gas or vapor sensing instrument (12), as shown in FIG. 5, includes the sensor cell assembly (19), potential-control circuitry (13), power supply (16), and the microprocessor (14) with the data acquisition-recording unit. The sensing instrument (12) is preferably battery operated, and has the ability to sample the gas or vapor and temperature signals at intervals and store in the random access memory (RAM) on the data acquisition board days to weeks of data. The data acquisition circuit microprocessor is programmed to sample and store the gas concentration signals at preset intervals. Data are off-loaded to a personal computer by accessing the microprocessor through an RS232 port.

The sensor cell assembly (19) and its potential-control circuit (13) are integrated with a battery-operated microprocessor (14) of 32 K memory, which samples the sensor signal as well as temperature and other signals at 10-, 20-, or 30-second intervals and stores an average value at intervals of 2, 5, or 10 minutes according to a programmable protocol. The data acquisition/storage unit in the microprocessor (14) can record 8 days of data, storing at 2-minute intervals, or up to 40 days storing at 10-minute intervals. In clinical testing to date, a 2-minute interval is suitable for one-day clinical studies and a 10-minute interval is appropriate for extended use. The microprocessor (14) with data acquisition/logic circuit can be programmed to sample more than one analog signal from the control circuit (13), and to convert these to digital signals and store them (i.e., gas concentration and temperature) at preset intervals together with real-time data. Data are off-loaded to a personal computer by accessing the microprocessor (14) through an RS232 port. After downloading, the digital data are converted to engineering units of gas concentration and temperature, and can be graphed by a menu-driven Lotus® 123 spreadsheet. Through a potentiometer in the gain amplifier circuit (15c), the device can be calibrated with calibrated gas samples, to indicate gas concentrations in the ambient.

The potential-control circuit (13) shown in FIG. 4 is powered, in a preferred embodiment, by six 1½ volt AA-size batteries (16d). A typical microprocessor (14) with data acquisition-recording capability that has been successfully used is sold by ONSET Computers, Falmouth, Mass., under the product name of "Tattletale Lite®." The sensor cell assembly (19) with its control circuit (13) is also designed to yield a current or voltage signal proportional to gas flux that could be used to continuously transmit the data to a remote receiving device or central monitoring station or unit.

The sensing electrodes can be organized in multiple arrays or sets containing a necessary number of counter or reference electrodes. Reference electrodes such as Pt/air ($O_2$), $PtO_2$, or dynamic hydrogen electrode as described by Giner (1964) may be employed. Electrically driven 3- or 2-electrode film type configurations may be employed using potentiostatic or potentiodynamic control of the potential of the sensing electrode (6). While the potentiostatic technique is a steady-state measurement, the potentiodynamic technique is a transient-type measurement method. In practice, the potentiodynamic process consists of four basic steps: a) hold sensing electrode potential constant with respect to the reference electrode to form a well-defined oxide layer; b) place the sensing electrode at open circuit to react the oxide layer with the gas for a pre-determined time, during which the sensing electrode rest potential shifts, depending on reactant concentration; c) resume potentiostatic control of the sensing electrode, changing the potential back to the initial potential and electrochemically regenerating the oxide layer; and d) measure the current (or charge) necessary to regenerate the oxide layer. The primary advantages of the potentiodynamic method are increased sensitivity, specificity, and stability. Two-electrode configurations require a reversible or stable counter-reference electrode such as Pt/air ($O_2$), $PtO_2$ or $Pt/H_2$ which has a higher BET (Brunauer, Emmett, Teller) surface area (25 $m^2/g$ or larger) and/or larger geometric surface areas than the sensing electrode.

Electrochemically reversible electrodes may be used in 3 or 2 electrode configurations, but especially in a 2 electrode arrangement where the counter electrode also acts as a reference electrode. Electrochemically reversible electrodes are constructed of stable catalyst materials and usually have a relatively large electrochemical active surface area so that they remain stable and their potential is not perturbed by small current flow. Examples include $PtO_2$ and Ag/AgCl electrodes.

The invention claimed is:

1. A sensor cell for detecting gases comprising:
   a substrate having a first surface and an opposite second surface;
   a sensing electrode; said sensing electrode in contact with said second surface;
   an opening extending from said first surface to said second surface proximate to said sensing electrode for controlling a gas flow; and
   a gas diffusion membrane in contact with and extending from said first surface to said sensing electrode, wherein said gas diffusion membrane has a thickness less than said substrate at said opening.

2. The sensor cell of claim 1 whereby said gas diffusion membrane is humidified by an aqueous material.

3. The sensor cell of claim 1 incorporated into a gas sensing instrument.

4. The sensor cell of claim 1, further including a counter electrode.

5. The sensor cell of claim 4 wherein said sensor cell is electronically controlled in a 2 electrode sensor configuration.

6. The sensor cell of claim 4, further including a reference electrode.

7. The sensor cell of claim 6 whereby at least one of said sensing, counter, or reference electrodes contains a fluorocarbon-bonded particulate catalyst which is bonded to an ionomer membrane.

8. The sensor cell of claim 7 whereby said fluorocarbon-bonded particulate catalyst is coated with said gas diffusion membrane where said gas diffusion membrane is polymeric.

9. The sensor cell of claim 6 whereby at least one of said sensing, counter, or reference electrodes contains an ionomer-bonded particulate catalyst which is bonded to an ionomer membrane.

10. The sensor cell of claim 9 whereby said ionomer-bonded particulate catalyst is coated with said gas diffusion membrane where said gas diffusion membrane is polymeric.

11. The sensor cell of claim 6 wherein said sensing, counter, and reference electrodes comprise a material selected from the group consisting of Pt, Au, C, platinized Pt, and platinized Au.

12. The sensor cell of claim 6 wherein said sensor cell is electronically controlled in a 3 electrode sensor configuration.

13. The sensor cell of claim 6 wherein said sensor cell is electronically controlled by a potentiostatic circuit connected to said sensing, counter and reference electrodes.

14. The sensor cell of claim 6 wherein said sensor cell is electronically controlled by a potentiodynamic circuit connected to said sensing, counter and reference electrodes.

15. The sensor cell of claim 1 wherein said sensor cell is electronically controlled by a constant voltage source connected to said sensing electrode and an electrochemically reversible counter electrode also acting as a reference electrode.

16. The sensor cell of claim 1 further comprising a microprocessor for real time data readout, data storage and retrieval, and remote data transmission.

17. A sensor cell for detecting gases comprising:
a substrate having a first surface and an opposite second surface;
a sensing electrode; said sensing electrode in contact with said second surface;
an opening extending from said first surface to said second surface proximate to said sensing electrode for controlling a gas flow; and
a gas diffusion membrane being of polymeric material in contact with and extending from first surface to said sensing electrode, wherein said gas diffusion membrane has a thickness less than said substrate at said opening.

18. The sensor cell in claim 17, wherein said gas diffusion membrane is a non-electrolytic material.

19. The sensor cell of claim 17, wherein said gas diffusion membrane is made of polyethylene.

* * * * *